(12) United States Patent
Lindegren et al.

(10) Patent No.: US 10,829,423 B2
(45) Date of Patent: Nov. 10, 2020

(54) AUTOMATIC PROCESS PLATFORM FOR THE PRODUCTION OF ASTATINE-211 [AT 211] RADIOPHARMACEUTICALS

(71) Applicant: Alpha Therapy Solutions AB, Gothenburg (SE)

(72) Inventors: Sture Lindegren, Kungsbacka (SE); Emma Aneheim, Gothenburg (SE)

(73) Assignee: Alpha Therapy Solutions AB, Gothenburg (SE)

(*) Notice: Subject to any disclaimer, the term of this patent is extended or adjusted under 35 U.S.C. 154(b) by 153 days.

(21) Appl. No.: 15/530,265

(22) PCT Filed: Jun. 17, 2015

(86) PCT No.: PCT/SE2015/050714
§ 371 (c)(1),
(2) Date: Dec. 16, 2016

(87) PCT Pub. No.: WO2015/195042
PCT Pub. Date: Dec. 23, 2015

(65) Prior Publication Data
US 2018/0215680 A1     Aug. 2, 2018

Related U.S. Application Data

(60) Provisional application No. 62/013,678, filed on Jun. 18, 2014.

(51) Int. Cl.
*A61K 51/10* (2006.01)
*C07B 59/00* (2006.01)
*G21G 1/00* (2006.01)

(52) U.S. Cl.
CPC ........ *C07B 59/008* (2013.01); *A61K 51/1045* (2013.01); *A61K 51/1051* (2013.01); *C07B 59/00* (2013.01); *G21G 1/001* (2013.01); *C07B 2200/05* (2013.01); *G21G 2001/0094* (2013.01)

(58) Field of Classification Search
None
See application file for complete search history.

(56) References Cited

U.S. PATENT DOCUMENTS

| | | | |
|---|---|---|---|
| 4,826,672 A | 5/1989 | Milius et al. | |
| 2002/0155063 A1* | 10/2002 | Wilson | C07B 59/00 424/1.11 |
| 2011/0150714 A1* | 6/2011 | Elizarov | B01J 19/0093 422/159 |

FOREIGN PATENT DOCUMENTS

| | | | |
|---|---|---|---|
| DE | 4239344 A1 * | 6/1993 | ............... B23Q 1/34 |
| EP | 0 203 764 A2 | 3/1986 | |
| EP | 1 237 584 B1 | 4/2011 | |
| WO | 91/09626 A1 | 7/1991 | |
| WO | 03/064678 A2 | 8/2003 | |
| WO | 2005/003151 A2 | 1/2005 | |
| WO | 2005/014052 A1 | 2/2005 | |
| WO | 2007/120251 A2 | 10/2007 | |
| WO | 2010/021719 A1 | 2/2010 | |
| WO | 2011/006032 A2 | 1/2011 | |

OTHER PUBLICATIONS

Schwarz, U.P., et al., "Preparation of 211At-Labeled Humanized Anti-Tac Using 211At Produced in Disposable Internal and External Bismuth Targets" Nuclear Medicine and Biology, 1998, pp. 89-93 (Year: 1998).*
Shao, X., et al., "Highlighting the Versatility of the Tracerlab Synthesis Modules. Part 1: Fully Automated Production of [18F] Labelled Radiopharmaceuticals using a Tracerlab FXFN", J. Labelled. Comp. Radiopharm., pp. 292-307 (Year: 2012).*
Speranza, A., et al., "Fully automated synthesis procedure of 4-[18F]fluorobenzaldehyde by commercial synthesizer: Amino-oxi peptide labelling prosthetic group", Applied Radiation and Isotopes, pp. 1664-1669 (Year: 2009).*
Gmelin Handbook, "Gmelin Handbook of Inorganic Chemistry", Springer-Verlag, pp. 199-200 (Year: 1985).*
Bakr,H.H.; ":Accurate activity determination of the aplha emitters Astatine 211At and Bistmuth 213Bi" (Goteborgs University Thesis, pp. 1-33; Jun. 9, 2014) (Year: 2014).*
DE4239344A1 Translation, accessed from: https://patents.google.com/patent/DE4239344A1/en?oq=DE4239344A1; accessed on Dec. 8, 2019, pp. 1-5 (Year: 2019).*
Lindegren, S. et al., Direct Procedure for the Production of 211 At-Labeled Antibodies with an e-Lysyl-3-(Trimethylstannyl) Benzamide Immunoconjugate, J. Nucl. Med 2008; 49:1537-1545.
Vaidyanathan, G., et al., Astatine Radiopharmaceuticals: Prospects and Problems, Curr. Radiopharm. Sep. 1, 2008; 1(3): 177.
Bhojani, M.E., et al., Synthesis and Investigation of a Radioiodinated F3 Peptide Analog as a Spect Tumor Imaging Radioligand, PLoS ONE 6(7): e22418, Jul. 2011.

* cited by examiner

Primary Examiner — Michael G. Hartley
Assistant Examiner — Lance W Rider
(74) Attorney, Agent, or Firm — Myers Bigel, P.A.

(57) ABSTRACT

A system and method for automatic production of astatine-211 labeled molecules is described. The invention represents a significant advantage in the preparation of At-211 radiopharmaceuticals including better reproducibility, reduced production time and increased radiation safety. The invention also enables routine automatic synthesis of radiopharmaceuticals in a clinical setting, in conjunction or at short distance from a cyclotron unit capable of producing the radionuclide.

3 Claims, 9 Drawing Sheets

FIG. 2A:1
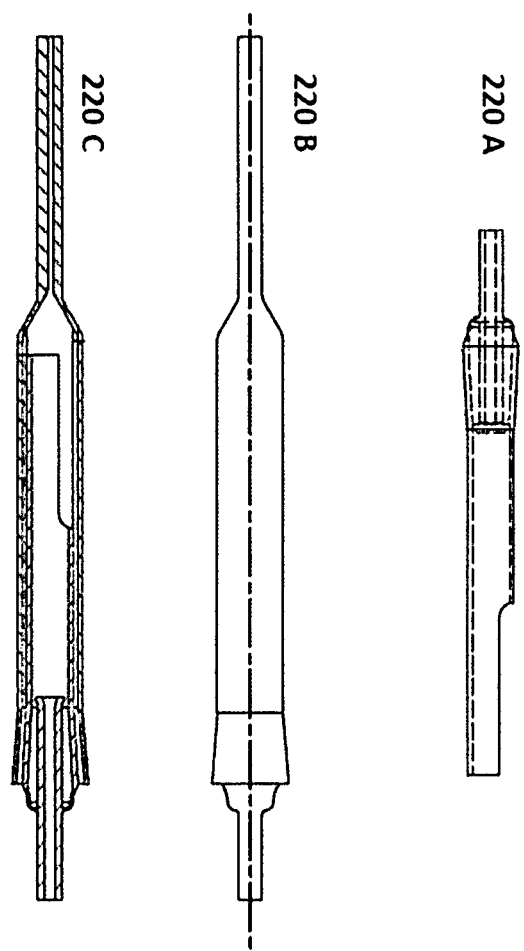

AUTOMATIC PROCESS PLATFORM FOR THE PRODUCTION OF ASTATINE-211 [AT 211] RADIOPHARMACEUTICALS

RELATED APPLICATION

The present application claims priority to U.S. Application Ser. No. 62/013,678, filed Jun. 18, 2014, the disclosure of which is incorporated by reference in its entirety.

FIELD OF THE INVENTION

The invention relates to a process for production of At-211-labelled molecules or radiopharmaceuticals comprising dry-distilling At-211, obtained from an irradiated bismuth metal target, in a quarts furnace, and introducing At-211 into a reaction vial and the subsequent chemical steps, including synthesis and purification, for a final astatinated product.

The invention also relates to a system for controlling a process for production of At-211-labelled molecules.

BACKGROUND OF THE INVENTION

The alpha-emitting radionuclide At-211 is one of few alpha-emitting radionuclides that have suitable properties for nuclear medicine applications, and particularly for treatment of undetectable microscopic cancer. Several preclinical studies utilising At-211 for therapy of micro metastasis have been conducted, including the free halide (i.e. astatide), and At-211-labeled tumour specific carrier vectors e.g. proteins or peptides. Many of these studies include tumor specific monoclonal antibodies, as they can be produced with binding properties to tumor-associated antigens. Promising preclinical results have been obtained with astatinated antibodies and two phase I studies have emerged from these studies.

Astatine-211 is one of the rarest nuclides on earth and has to be synthesised artificially in a cyclotron, limiting its availability. Although the availability of the nuclide is sparse it has the potential to be produced in large quantities for prospective nuclear medicine applications. The general route for producing the nuclide is by irradiating stable bismuth with accelerated 28 MeV alpha-particles via the Bi-209(alpha,2n)At-211 nuclear reaction. There is no limitation in availability of Bi-209 for producing At-211, however, there are few medium energy cyclotrons around the world that presently have the means and the capacity for producing At-211 in amounts required for clinical applications. In addition to the current low availability of the nuclide the chemistry of astatine also presents challenges. After the irradiation, i.e. the cyclotron production, At-211 has to be converted to a chemically useful form. This can be done either by wet extraction or by dry distillation of the irradiated target material. Once in an appropriate chemical form, the At-211 can be subjected to chemical coupling reactions and further used as a component of radiopharmaceuticals.

The generally employed route of synthesis of astatinated bio-molecules such as proteins, antibodies and peptides is conducted in two steps; labeling of a reagent and conjugation of the labeled reagent to the bio-molecule. However, when using this strategy problems with yields and the final quality are frequently occurring and have been recognised being due to radiolytic effects within the reacting solvents. These problems are pronounced at high activity concentration reaction conditions where the alpha-decay of astatine during labeling may result in a significant absorbed dose to the reaction solvent. The high absorbed dose to the reaction mixture can affect the chemistry by oxidation of astatine, decomposition of the precursor and/or alteration of the structural and biological integrity of the bio-molecule. This can ultimately lead to e.g. the elimination of a carrier antibody's binding properties to its target. It has been reported that antibodies can be subjected to a maximum absorbed dose of approximately 1000 Gy without affecting its biological properties.

In order to overcome the problems with radiolysis a new route for synthesizing At-211 labeled bio-molecules such as proteins, antibodies and peptides has been developed. This route is similar to that of chelate chemistry, producing conjugate with the labeling reagent and the bio-molecule in advance to the radiolabeling. In this way only one radiochemical step is involved in the synthesis. This enables fast reaction kinetics, low dependence on concentration, improving specific radioactivity and radiochemical yields while maintaining structural and biological integrity of the bio-molecule. Using this strategy it is possible to manually produce the amount of activity required for clinical applications with At-211 labeled antibodies (Lindegren S, Frost S, Bäck T, Haglund E, Elgqvist J, Jensen H. (2008) Direct Procedure for the Production of 211At-Labeled Antibodies With an ε-dysyl-3-(trimethylstannyl)benzamide Immunoconjugate. J Nucl Med 49: 1537-1545).

Methods of related art also describes the manual production of astatine (Lindegren S., Bäck T. and Jensen H. J. (2001) Dry-distillation of Astatine-211 from Irradiated Bismuth Targets: A Time-saving procedure with High Recovery Yields. Appl. Radiat. Isot. 55), including synthesis of labeled intermediate compounds (WO 91/09626).

WO 91/09626 describes a process for radiolabeling and isolation of a small precursor with At-211. At-211 is dry-distilled in an oven and then from the oven directly introduced in a reaction vial, which comprises a precursor of a molecule adapted to bind At-211. In this process vaporized At-211 is passed through a reaction vial containing a cooled liquid with a precursor. The reaction is performed in a sequence of traps. A disadvantage of this method is low efficiency in the gas liquid solvation and that intense manual purification is needed of the labeled precursor after the reaction.

The reaction vial needs to be separated from the process unit to perform the purification steps. This decreases radiation safety and is time consuming.

Furthermore, no scraping of At-211 from the irradiated bismuth target is done. Thus, the At-211 is not dry-distilled as a powder-like material. This prolongs the time needed for dry-distillation, increases impurities in the vaporized At-211 that is introduced in the reaction vial and requires a large distillation system due to the size of the heated target. The process also produce an astatine labeled precursor that needs to be put through further manual synthesis steps in order to obtain a final At-211 labeled radiopharmaceutical product. This in turn means that additional manual purification of the product has to be performed.

For continued advancement of methods the field requires further development as the prior art suffers from method related deficiencies and drawbacks. The main drawback of the prior art is that it includes a series of different manual steps where the final result will depend on hands-on skills of the laboratory personnel. Although the manual synthetic route of synthesizing At-211 radiopharmaceuticals can be efficient, future progress of preclinical research and clinical advancement with At-211 is reliant on further improvements and developments of the radiochemistry. Particularly the method would benefit from being transferred from a stepwise manual method into a fully automatic procedure.

SUMMARY OF THE INVENTION

The invention describes a process for the radiosynthesis of astatinated radiopharmaceuticals e.g. proteins and peptides including converting At-211 from solid form in irradiated bismuth target material into a chemically useful form. In this way, the invention overcomes major hurdles in the prior art by providing a complete process for production of any At-211 labeled molecule or any At-211-radiopharmaceutical. The invention enables automatic, reproducible, fast, high yield production of clinically relevant amounts of At-211 and At-211-radiopharmaceuticals of clinical grade. It is an objective of the invention to provide a process and an automation method for automatic production of At-211 labeled molecules.

The objective is achieved by a process for production of At-211-labeled precursor molecules comprising
  dry-distillation of At-211 from irradiated Bi-213 target material in a furnace system (100, 101) and a synthesis unit The process is characterized in that the process comprises the steps of,
  A) condensing the dry-distilled At-211 by cooling in a cooling unit (106) to obtain At-211 as a dry residue.
  B) eluting the At-211 with a transfer liquid that solvate the dry residue of At-211, a) an organic solvent b) a solvent containing an oxidizing agent, or c) a solvent containing a reducing agent
  C) introducing At-211 for further chemical processing into said reaction vial
  D) activating At-211 for further chemical processing a) At-211 in an organic solvent in to an empty vial for further chemical steps, or b) oxidized At-211 in a vial containing a precursor molecule for reaction with At-211, and further chemical steps, or c) oxidized At-211 into an empty vial for further chemical steps, or d) reduced At-211 into an empty vial for further chemical steps The new process of isolating and converting At-211 into a chemically useful form is more efficient and effective compared to known processes. The preparation time is reduced using the new process. Further, less by-products are obtained and thus, less time for purification is needed. The yield of the product in this process is increased.

The process provides for an automatic synthesis from isolation of the At-211 nuclide from irradiated Bi-209 target material to the full synthesis product enabling automatic production of purified astatinated radiopharmaceuticals. The system is versatile and can be adapted in different embodiments to meet a specific aim in the automatic production of At-211, and At-211 labeled compounds.

No manual interruption is needed in the process. Thereby, the safety and the reproducibility is also improved.

In one embodiment, the At-211 is obtained by scraping an irradiated bismuth target to an At-211 powder target material and whereby in the scraping is performed using a scraping unit (120). An advantage of scraping is that an At-211 containing powder-like material, said At-211 powder (125) is obtained. The surface area of this particulate material is larger compared to the surface area of layers of sandwiched bismuth and aluminum. This decreases the time needed to vaporize At-211 in the furnace and thus improves the efficient and effective of the process. The volume of this metal particle material is also smaller than that of sandwiched bismuth and aluminum. This may reduce the size of the distillation equipment needed, which is beneficial.

In another embodiment, a transfer liquid is used to elute At-211. The transfer liquid is an organic solvent. The same transfer liquid may not always be suitable as a solvent in a reaction with a precursor molecule. In some cases, it may be necessary or preferred to exchange the transfer liquid with another solvent.

In one embodiment the transfer liquid is an adaptive solvent oxidizing At-211.

In another embodiment the organic solvent is evaporated leaving a dry residue of At-211. This embodiment increases the flexibility of the process through the ability to vaporize the transfer or elution liquid. The solvent used in the reaction vial can thus be varied and adapted to the precursor molecule and its solvent.

In a further embodiment, an inert gas is used to transport dry-distilled At-211 from the furnace system to the cooling unit and transfer liquids and solvents through the system. In one embodiment, the inert gas is selected from the group comprising nitrogen, argon, helium, and mixtures thereof. A vacuum pump is used to provide an underpressure through the capillary system used to perform the process. The underpressure causes the inert gas to be contained within and flow through the platform or system at which the process is performed. Containing the inert gas and hence the volatilized astatine in the system minimize activity loss and increase radiation safety.

In another embodiment, a prompt reduced pressure is applied to confine At-211 in the system. The final reduced pressure is achieved within 10-30 seconds to increase the rate of the dry-distillation process of the system. In this way the dry-distillation can be terminated after 10-30 seconds. This much shorter distillation time compared to previous processes minimizes the activity loss caused by radioactive decay of At-211.

In one embodiment the transfer liquid and the dry distilled At-211 is passed through the same three way valve, in different settings, placed before the cooling unit. This feature of the system is beneficial as it opens the possibility for using any eluting solvent for transferring At-211 for further automatic chemical processing. The introduction of a three way valve in this position also allows for high distillation yields without any manual interference.

In one embodiment, the cooling unit is a cryotrap that indirectly cools the astatine condensation capillary with a cooling media, such as, but not limited to, liquid nitrogen. In this way vaporized At-211 can be effectively isolated from the bismuth/aluminum particulate target material, said At-211 powder, and captured as a dry residue.

In another embodiment a heat transfer insertion, around which the astatine condensation capillary is coiled, made of a heat conducting material such as aluminum is introduced into the cryotrap. Efficient cooling of the astatine condensation capillary as with the use of a cryotrap with heat transfer insertion and especially the use of one single capillary without connections from the three way valve to the reaction vial greatly reduce astatine loss.

In a further embodiment, cooling temperature in the cooling unit is between −20 and −60° C. The temperature range given prevents loss of volatilized astatine from the cooling unit, increasing yields and radiation safety while maintaining the possibility to use multiple solvents for astatine transfer without causing freezing, blocking the capillary system.

In a further embodiment, the transfer liquid is an organic solvent. The transfer liquid is preferably a liquid in which At-211 dissolves. The transfer liquid is preferably compatible with the precursor molecule and the solvent.

In one embodiment, the transfer liquid is selected from the group comprising chloroform, acetic acid, sodium hydroxide, methanol, ethanol, N-iodosuccinimide, N-bromosuccinimide, N-chlorosuccinimide, and mixtures thereof.

The versatility of transfer liquids allows the production of a range of astatinated radiopharmaceuticals with the same process platform.

In one embodiment, At-211 is in one or more redox forms selected from the group comprising At-211° (ground state), At-211$^{n-}$ (reduced form) and At-211$^{m+}$ (oxidized form). This may or may not be as an interhalogen compound e.g. [$^{211}$At]AtX or [$^{211}$At]AtX$_2^-$, X=Cl or I.

In another embodiment the process can be used for the production of astatine labeled bio-molecules by activating At-211 for further chemical processing according to, E) reacting activated At-211 with a precursor molecule
F) purifying astatinated molecules from unreacted species in the reaction mixture
and optionally, G) sterile filtering the purified product In one embodiment, the precursor molecule is selected from the group comprising inorganic molecules, organic molecules such as non-proteins, proteins, peptides, antibodies or fragments thereof, and modifications and mixtures thereof.

In one embodiment the reaction of a precursor molecule, is completed within 0.5-5 minutes. The short reaction times for At-211 labeling in this system result in low absorbed dose to the reaction mixture. This means that the precursor molecules will not be exposed to detrimental or harmful radioactive doses.

In another embodiment the system is clinically validated, the system being approved for producing radiopharmaceuticals ready for use in humans. The new process can thus be used to provide products that can be used for diagnostic or therapeutic treatments in humans. In one embodiment, the process is employed for producing clinical grade At-211 radiopharmaceuticals e.g. At-211-labeled antibodies or At-211-labeled peptides with high chemical and radiochemical purity (>98%).

In one embodiment, steps A to G are performed at room temperature. In another embodiment, one or more steps are performed at room temperature. Although the temperatures at which the different steps are performed can easily be varied, it is economically advantageous to perform most of the steps of the process at room temperature. This also makes upscaling of the process more feasible.

In a further embodiment, the purification step is performed using liquid chromatography or high pressure liquid chromatography. This allows for removal of free At-211 and/or unreacted reagents from the product mixture.

In another embodiment a liquid chromatography column in the purification step comprising either a) a size exclusion column (SEC), or b) an adsorption chromatography column, or c) a partition chromatography column, or d) an ion exchange chromatography column, or e) an affinity chromatography column. This enables the production of a pure final product regardless of which precursor molecule that is introduced into the system In one embodiment, the process is controlled by a control unit (140), including a computer with software (130)

In one embodiment the complete synthesis route, from distillation of the irradiated Bi-209 target material to a purified At-211 labeled product, is performed in a fully automated production system. This fully automatic system provides better reproducibility as it reduces the risk for human error, reduces the need for specialist competence in the operation and increases radiation safety compared to a system with manual handling. At least 85% (non-decay corrected) of initial At-211 radioactivity input into the distillation unit is routinely recovered in the distillation process and an overall radiochemical yield of 50% (non-decay corrected) of initial At-211 radioactivity input into the distillation unit is routinely recovered in the complete synthesis process.

In one embodiment the product produced by the fully automated system is either At-211 or an astatinated inorganic molecule or organic molecule such as non-proteins, proteins, peptides, antibodies or fragments thereof a) organic molecule b) peptide c) protein d) radiopharmaceutical of a) to c). The versatility of the product of the automatic system allows it to be used both in preclinical research as well as in the production of different astatinated radiopharmaceuticals for clinical use, which would require several different manual systems and competences.

In one embodiment the process is monitored by radiation detectors in conjunction with the control unit. Monitoring the radioactivity allows for following the At-211 through the system as well as the At-211 labeled molecule, from distillation to labeling and finally purification. This gives an increased control of the process.

In another embodiment the radioactivity is quantified using calibrated radioactivity detectors. This enables direct estimation and evaluation of distillation-, labeling- and overall process yields.

In another embodiment of the automatic system the process is completed after automatic distillation, condensation and elution of At-211, the product being a) At-211 in an organic solvent, or b) At-211 of dry residue after automatic evaporation of the solvent In another embodiment of the automatic system the process is completed after purification and optionally sterile filtration of an At-211 labeled molecule.

In one embodiment the process platform is, except from the system control unit, including computer with software, assembled in a glovebox. By isolating the automatic system, At-211 radioactivity is confined throughout the complete process from distillation to purified At-211 compound or radiopharmaceutical. In this way the automatic process will increase safety reducing the exposure of At-211 radioactivity of the personnel.

The objective is also achieved by a system for automatically controlling a process for production of At-211-labeled molecules.

The system comprises:
a quartz glass receptacle (100) for receiving a powder of At-211,
a furnace (101) for vaporization of the At-211 powder by heating the receptacle,
a cooling unit (106) for condensing the vaporized AT-211 to obtain At-211 as a dry residue,
a transfer liquid container (107) containing a transfer liquid for eluting the At-211,
a reaction vial (109) for further chemical processing of the At-211,
a capillary system including a plurality of capillaries (104, 108) for transportation of the vaporized At-211 to the cooling unit (106) and further to the reaction vial (109), and for transportation of the transfer liquid from the liquid container (107) to the cooling unit, a vacuum pump (201) arranged to reduce the pressure in the capillary system (104) to achieve an underpressure in the capillary system for transportation of the At-211 and the transfer liquid, a gas flow device (208) arranged to introduce a gas flow into the capillary system for assisting in transportation of the At-211 and the transfer liquid, one or more radioactive detectors (400, 401, 402) for measuring the radioactivity at one or more locations in the system, and a control unit (140) configured to control the transportation of the At-211 and the transfer liquid in the capillary system by generating control commands to the vacuum pump and the gas flow device based on input data from the radioactive detectors corresponding to measured radioactivity at said one or more locations in the system.

The system makes it possible to automatically control a process for production of At-211-labeled molecules.

By measuring the radioactivity in one or more locations in the system it is possible to estimate the present amount of At-211 in a certain part of the system. The control unit can then decide whether the amount of At-211 in the certain part of the system is acceptable or not. If the amount of At-211 in the certain part of the system is not acceptable, the control unit may increase or decrease the transportation of the At-211 and transfer liquid in the capillary system by adjusting the gas flow and the pressure in the capillary system. If the amount of At-211 in the certain part of the system is acceptable, the gas flow and the pressure in the capillary system is maintained. Thus, the gas flow and the pressure in the capillary system is adjusted based on input data from the radioactive detectors so that the process for production of At-211-labeled molecules is maintained.

The system is suitable for controlling the process according to claim 1.

The control unit comprises hardware as well as software for controlling the process. The control unit comprise input and output means, processing means, for example, a central processing unit (CPU), a FPGA or similar hardware, and memory means, such as ROM and RAM, and software modules for generating control commands to the to the vacuum pump and the gas flow device. The control unit is configured to receive data, such as measuring values, from the radioactive detectors. The control unit may include a computer.

In one embodiment, the control unit is configured to generate the control commands to the vacuum pump (201) and the gas flow device (208) based on the input data from the radioactive detectors (400, 401, 402) and predefined limit values for the radioactivity at said locations in the system. The limit values can, for example, be determined based on experiments and/or empirical data. The limit values may vary over time during the process. Thus, the limit value may represent a desired amount of At-211 at a certain location at a certain point in time.

In one embodiment, a first radioactivity detector (401) is disposed in the vicinity of the cooling unit (106), and a second radioactivity detectors (400) is disposed in the vicinity of the reaction vial (109). Thus, the input data from the first radioactive detector corresponds to the measured radioactivity in the vicinity of the cooling unit, and accordingly to the amount of At-211 present in the vicinity of the cooling unit, and the input data from the second radioactive detector corresponds to the measured radioactivity in the vicinity of the reaction vial, and accordingly to the amount of At-211 present in the vicinity of the reaction vial.

In another embodiment, a third radioactivity detector (402) is disposed in the vicinity of the product vial (118). Thus, the input data from the third radioactive detector corresponds to the measured radioactivity in the vicinity of the product vial, and accordingly to the amount of At-211 present in the vicinity of the product vial.

In another embodiment, one of the radioactivity detectors (404) is disposed in the vicinity of the of the quartz glass receptacle (100), or more particularly in the vicinity of the inlet to the receptacle (102). Thus, it is possible to estimate the amount of At-211 present at the inlet of the system. This activity detector would also allow for an automatic start of the process without manual input, upon insertion of the At-211 containing target material into the furnace system (100, 101).

In another embodiment, another radioactivity detector (403) is disposed in the vicinity of the purification column (113). Thus, the input data from this radioactive detector corresponds to the measured radioactivity in the vicinity of the purification column, and accordingly the amount of At-211 present in the vicinity of the purification column. This makes it possible to estimate the At-211 labeling yield of the precursor molecule.

In one embodiment, the system further comprises at least one pressure sensor for sensing the pressure in the capillary system, and the control unit (130, 140) is configured to generate the control commands to the vacuum pump (201) based on input data from the radioactive detectors and input data from the at least one pressure sensor. The control unit may decide a desired pressure for controlling the process based on input data from the radioactive detectors, and to determine how to control the vacuum pump to achieve the desired pressure based on the measured pressure, i.e. whether the pressure in the capillary system is to be increased, decreased or maintained.

In one embodiment, whereby in the system further comprises at least one flow sensor (302) for sensing the flow in the capillary system and the control unit (140) is configured to generate the control commands to the gas flow device based on input data from the radioactivity detectors and input data from at least one flow sensor.

In another embodiment, the system further comprises reagent container (111) containing a reagent, and the capillary system further comprises a capillary (112) for transportation of reagent from the reagent container (111) to the reaction vial (109), and the control unit (140) is configured to control the transportation reagent in the capillary system by generating control commands to the vacuum pump and the gas flow device based on input data from the radioactive detectors.

BRIEF DESCRIPTION OF DRAWINGS

The foregoing and other aspects of the present invention will now be described in more detail with reference to the following figures.

FIG. 2A:1 schematically illustrates one embodiment of a detail in FIG. 2

DETAILED DESCRIPTION OF PREFERRED EMBODIMENTS

It should be appreciated that the invention may be embodied in different forms and should not be construed as limited to the embodiments set forth herein.

The terminology used in the description of the invention herein is for the purpose of describing particular embodiments only and is not intended to be limiting of the invention. As used in the description of the embodiments of the invention, the singular forms "a," "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. When a range is employed (e.g., a range from x to y) it is it meant that the measurable value is a range from about x to about y, or any range therein, such as about $x_1$ to about $y_1$, etc. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

All patents, patent applications and publications referred to herein are incorporated by reference in their entirety. In the event of conflicting terminology, the present specification is controlling. Further, the embodiments described in one aspect of the present invention are not limited to the aspect described. The embodiments may also be applied to a different aspect of the invention as long as the embodiments do not prevent these aspects of the invention from operating for its intended purpose.

Figure 5:
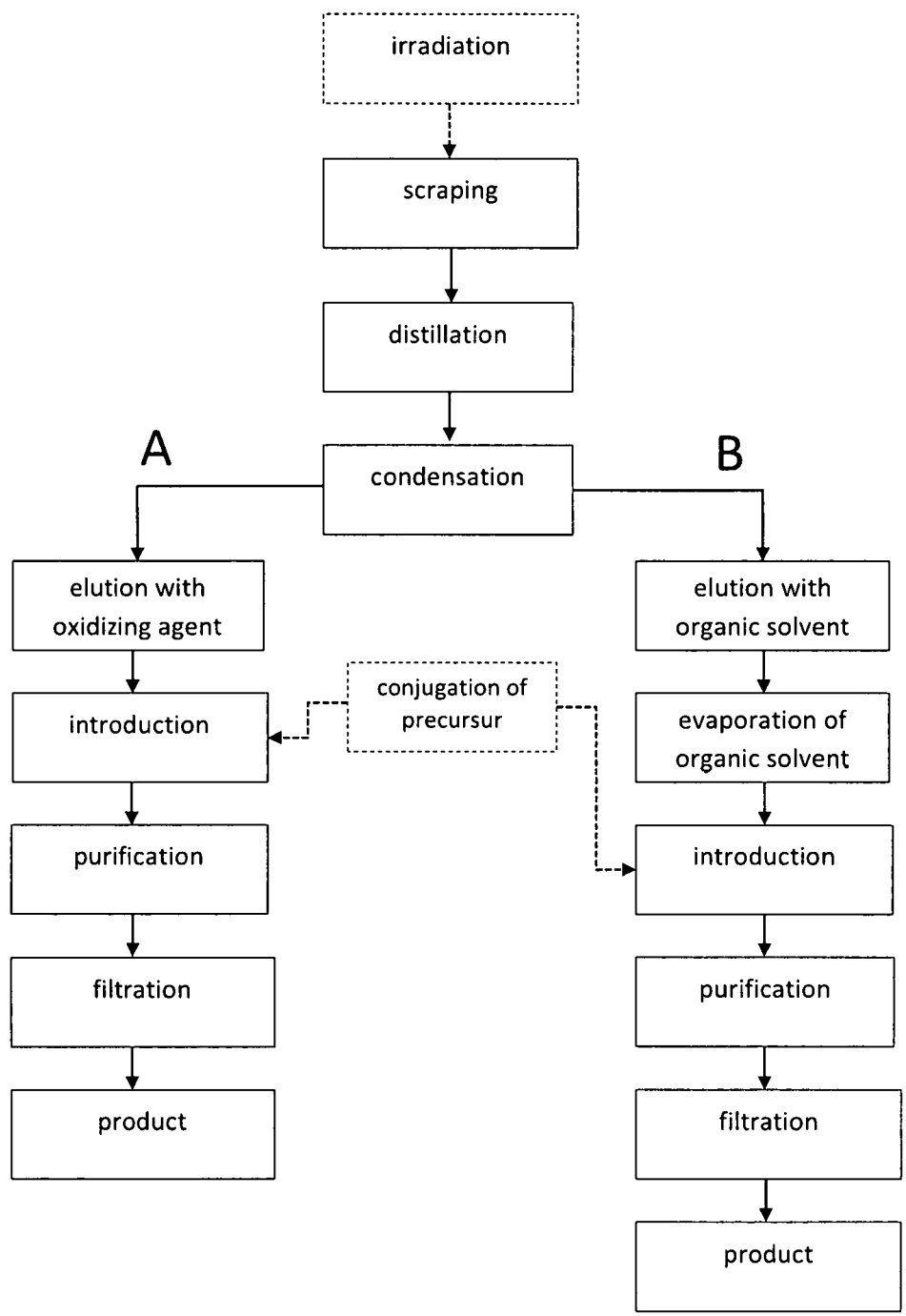

As shown in the flow chart of FIG. 5 the process comprises the following steps;
irradiate bismuth metal to obtain At-211,
scraping the obtained At-211 from the irradiated Bi-209 target,
introducing the At-211 powder-like material in a quartz glass receptacle
heating the At-211 with a furnace in order to vaporize the At-211,
transfer the vaporized At-211 to a cooling unit,
condense the At-211 by cooling to obtain a dry residue of At-211
add a solution, organic solvent (5B) or solvent with oxidizing or reducing agent (5A), and elute At-211 to a reaction vial
5B only, evaporate organic solvent
5B only, activate/oxidise the isolated astatine,
react the activated astatine with the precursor molecule, and
transport the obtained product to a purification unit,
purify the product in the purification unit,
transport the purified product to a filtration unit,
sterile filtrate the purified product, and
transport the pure, sterile product to a product vial.

Figure 1:
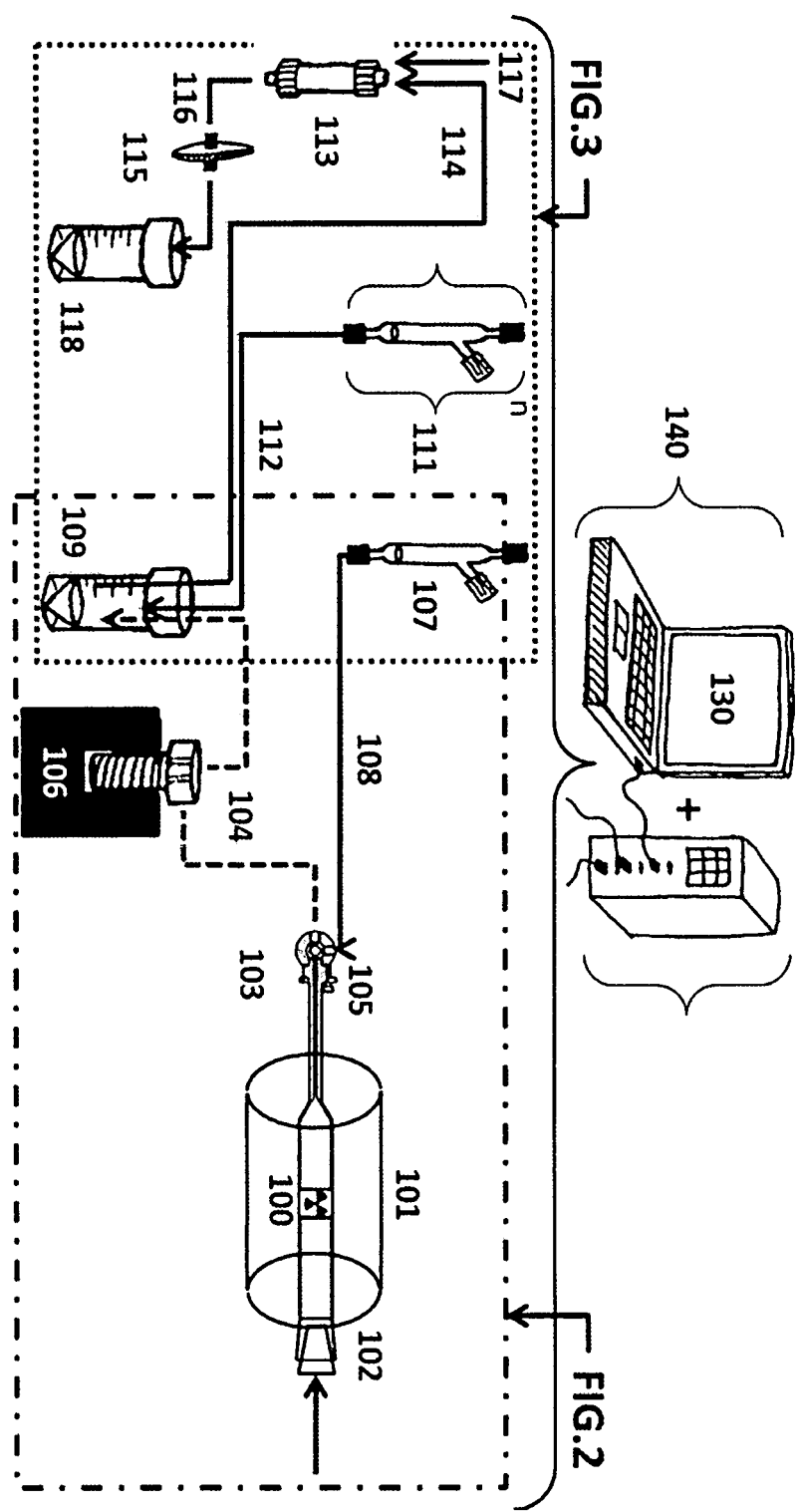
FIG. 1 schematically illustrates the software controlled automatic process platform assembly FIG. 1A schematic description of the scraping unit.
Figure 1A:
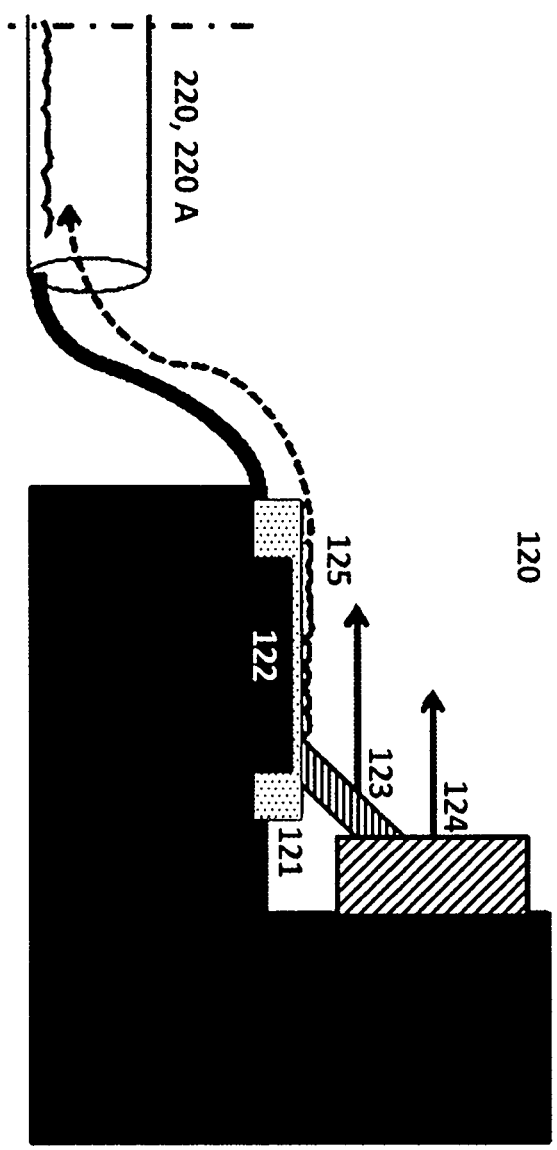

FIG. 1 shows a platform for performing the process of the invention. From a scraping unit (120, FIG. 1A), the irradiated At-211 is inserted into the quartz glass receptacle 100, heated by tube furnace 101, via inlet 102. After heating the vaporized At-211 leaves the oven through outlet 103 into condensation capillary 104 via three way valve 105 (in valve position 121, FIG. 2A). Astatine is condensed in condensation capillary 104 by the cooling unit 106. After condensation, a transfer liquid 107 is introduced to capillary 104, through a transfer liquid capillary 108, via a three way valve 105 (valve position 122, FIG. 2A). The eluted At-211 is transported to a reaction vial 109 through the condensation capillary 104 by the means of reduced pressure (from vacuum pump 201, FIG. 2) and inert gas flow (from gas flow device 208, FIG. 2). The precursor molecule is added to the reaction vial, preferably prior to the addition of At-211, depending on the nature of the transfer liquid, from a reagent container 111 via reagent capillary 112. After reacting, the obtained product is transported to a purification unit 113 via a purification capillary 114. After purification, the purified product is optionally transported to a filter unit 115 and filtration capillary 116 before reaching the final product vial 118. The whole process can be automated using control unit 140 including a computer (130) with software. The process steps may be performed at one or more temperatures. The process steps (outside the oven and after the cooling unit) may be performed at room temperature.

Elution of the condensation capillary 104 is performed using a transfer liquid, preferably an organic solvent, which allows for astatine capture in a reaction vial 109 in a chemically useful form. A chemically useful form may be defined as an interhalogenic compound with astatine e.g. [$^{211}$At]AtX or [$^{211}$At]AtX$_2^-$, X=Cl or I or At-211$^{n-}$ (reduced form) and At-211$^{m+}$ (oxidized form). The transfer liquid is transported from a transfer liquid container 107 through capillary 108 via a three way valve 105 to the condensation capillary 104, in the cooling unit.

Examples of transfer liquids, with or without added oxidant, may be chloroform, acetic acid, sodium hydroxide, methanol, ethanol or methanol or ethanol with N-bromo-, N-chloro- or N-iodo-succinimide, or mixtures thereof. In one embodiment, the transfer liquid is chloroform or methanol with N-iodo-succinimide.

Reagents for labeling, stored in reagent container(s) 111, including conjugated or non-conjugated precursor molecules as described below are added sequentially into the reaction vial.

Conjugated molecules (including peptides or proteins, antibodies or similar as non-limiting examples) are precursor molecule's for automatic labeling with At-211. The conjugated precursor molecule is synthesized prior to being processed in the automatic platform. The conjugate is preferably synthesized from a reaction with a targeting molecule and an intermediate bifunctional reagent. The bifunctional reagent preferably has a good leaving group for substitution with At-211 such as, but not limited to, organic tin, silane, or boron cage derivatives and a functional group e.g. succinimide or maleimide for binding to targeting molecule entities (for example protein, peptide, antibody or the like) such as amino or sulfhydryl groups.

Although the At-211 labeling reaction is efficient, the product must be separated from unreacted At-211. This feature of the platform is integrated in the radiopharmaceutical process, where the reagent mixture may be purified, preferably on a suitable chromatography column using a suitable buffer solution 117 for the purification. Different chromatography methods such as size exclusion chromatography, affinity chromatography, ion exchange chromatography or high pressure liquid chromatography (HPLC) may be used for purification. In this step the product is also purified from possible unreacted reagents. The purified product of the automatic process may be sterile filtrated 115 which filtration step is integrated as a final step.

The radioactive At-211 is produced in a cyclotron by the Bi-209(alpha,2n)At-211 nuclear reaction. The Bi-209 target for cyclotron production of At-211 is supported by a backing of e.g. aluminium or cupper. The irradiated target material may be a sandwich wherein a layer of bismuth is sandwiched between two layers of aluminium. The target material to be used can be put in the quartz glass receptacle, heated by a furnace to vaporize the At-211. Preferable, the target material is scraped from a backing i.e. the top layer of the sandwiched target prior to entering the target material into the quartz glass receptacle.

The target scraping is described in FIG. 1 A, and is performed in an automatic scraping unit 120. The target 121 is mounted and fixed in a target holder 122 of the scraping unit. The target is directed for scraping the target towards the irradiated area. When the target is fixed, a chisel 123 is set to scrape the top-layer of the target, the sandwich of irradiated Bi-209 layer and the thin top-layer of aluminium. The chisel is motor driven by an electric motor 124. The scraping, a powder-like target material, At-211 powder 125, is in one embodiment directed into a quartz glass container (220, FIG. 2A) and in another embodiment into a quart glass container which is joined with the inlet joint of the distillation glass (220 A, FIG. 2A:1). The chisel is started with a starting button and the chisel then slowly scrape the powder-like material into the quartz glass container. The scraping is preferably performed in direct conjunction to the distillation system.

Figure 2:
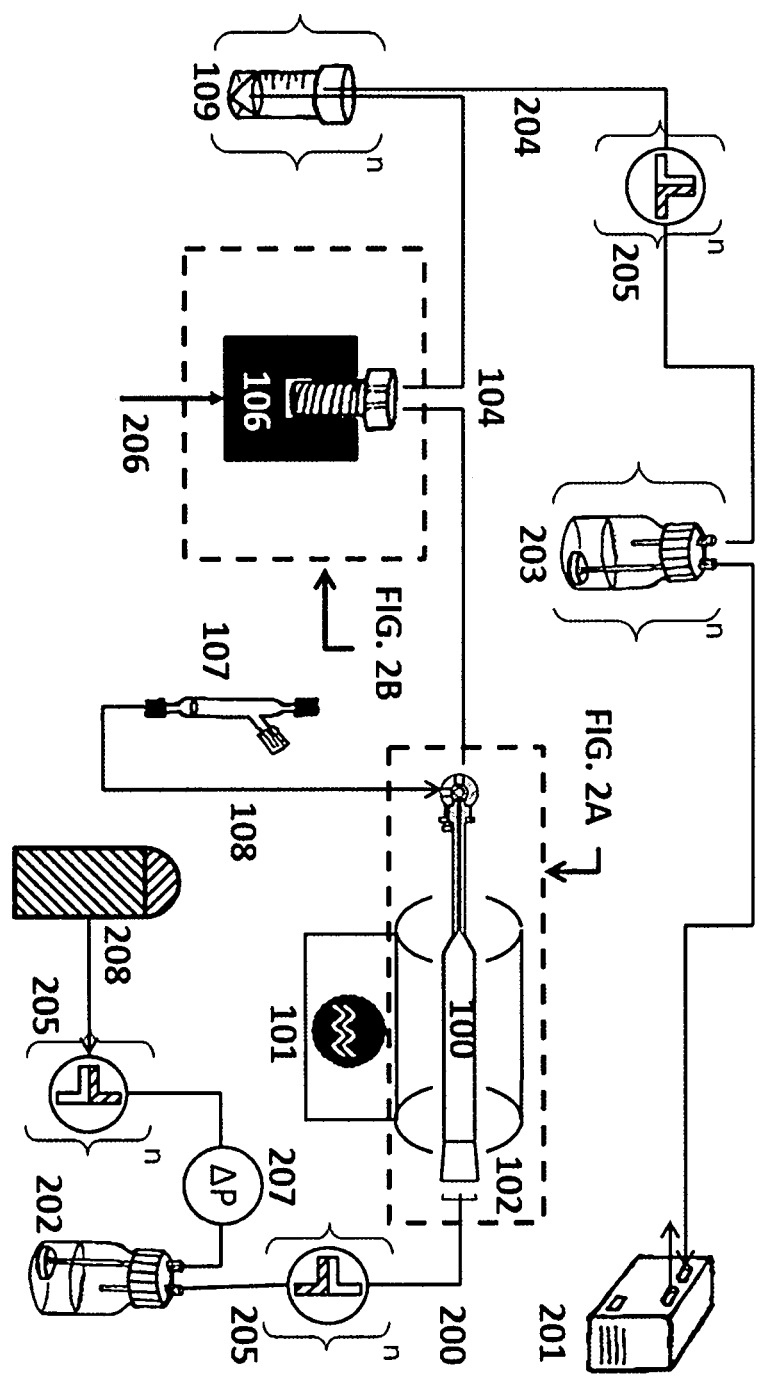
FIG. 2 schematically illustrates one embodiment of the automatic astatine distillation as part of the platform assembly illustrated in FIG. 1.
Figure 3:
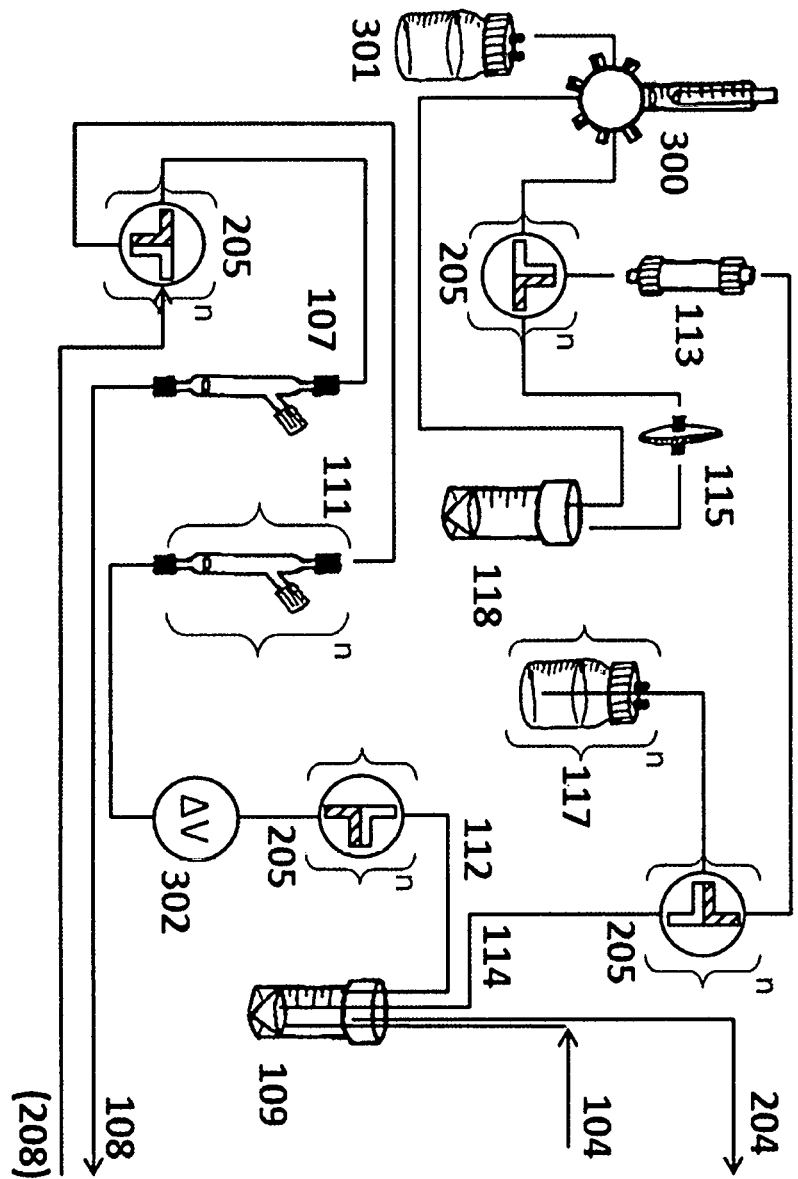
FIG. 3 schematically illustrates one embodiment of the automatic astatine labeling part of the platform assembly, illustrated in FIG. 1.
Figure 4:
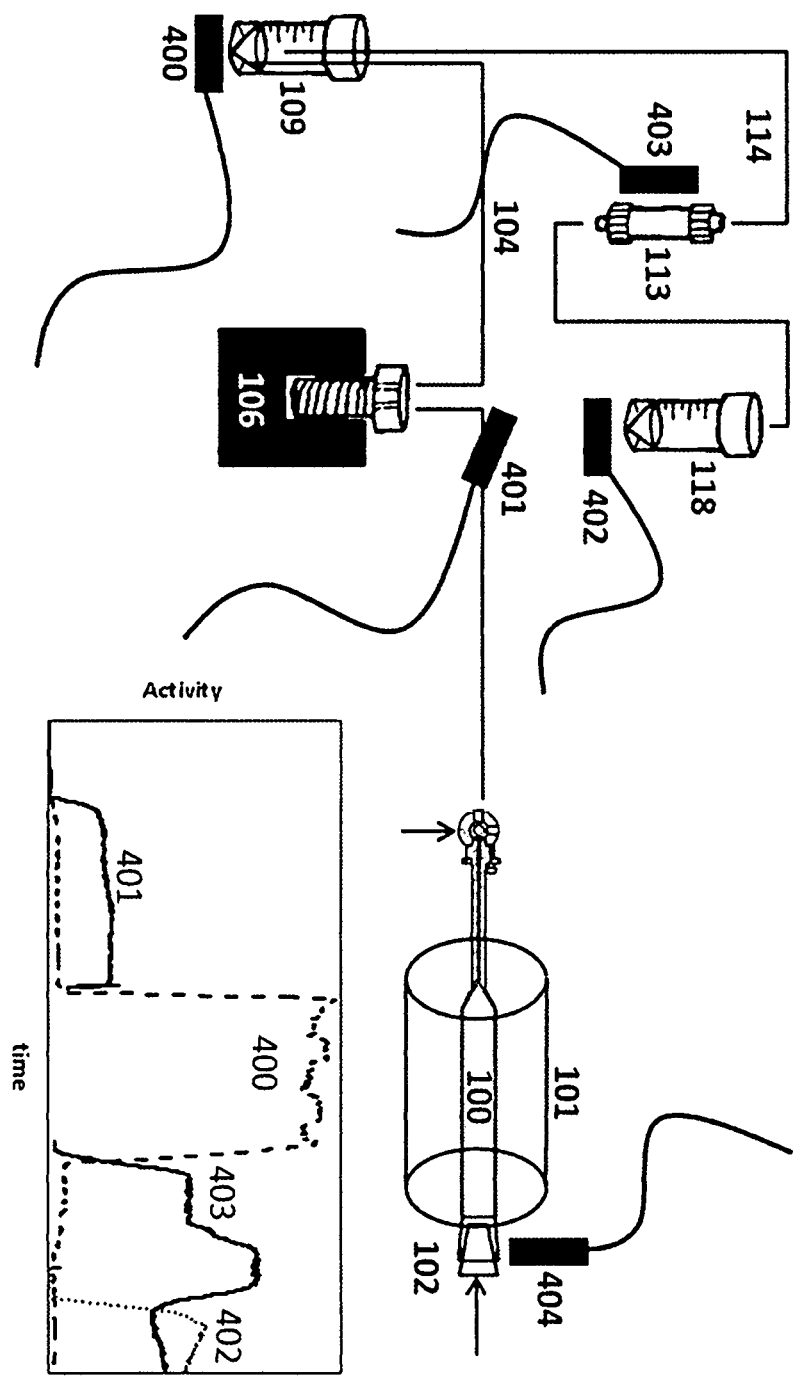
FIG. 4 schematically illustrates one embodiment of activity detectors used during distillation with the automatic process platform FIG. 5 show a flow chart for the process.

FIG. 2 to FIG. 4 show detailed aspects of the platform described above.

The overall distillation process is described in FIG. 2. After scraping, the powder-like material in the target material container insert is assembled with the quarts glass receptacle 100, through the oven inlet 102. A gas flow capillary 200 is provided in the oven for inlet of carrier gas. The oven outlet 103 is connected to a three way valve 105 in flow through position 221, which is connected to a condensation capillary 104 for transport and condensation of At-211. Condensation is enabled by the cooling unit 106. The quartz glass receptacle may be heated by the furnace 101 at a temperature between 400 and 900° C., or between 600 and 800° C. The vaporized astatine is transferred through the distillation system from the heated quartz glass receptacle 100 to the condensation capillary 104, cooled by cooling unit 106, using reduced pressure, measured by pressure sensor 207, created by a software controlled vacuum pump 201 and an inert carrier gas, such as, but not limited to, nitrogen, argon or helium. A controlled flow rate, from the gas flow unit 208, may be between 0.5 and 400 ml/min, preferably between 1 and 200 ml/min. The carrier gas is preferably dried before entering the system utilizing e.g. scrubbing though a moisture absorption media 202. The condensation capillary 104 is connected to a reaction vial 109 for collection of eluted astatine and synthesis. Several astatine traps 203 such as volume expansion and/or sulfite gas scrub can be employed to capture potentially over-distilled gaseous astatine prior to reaching the vacuum pump 201, connected via underpressure capillary 204. The system also encompasses n number of software controlled three way valves 205 for liquid and gas transport.

Figure 2A:
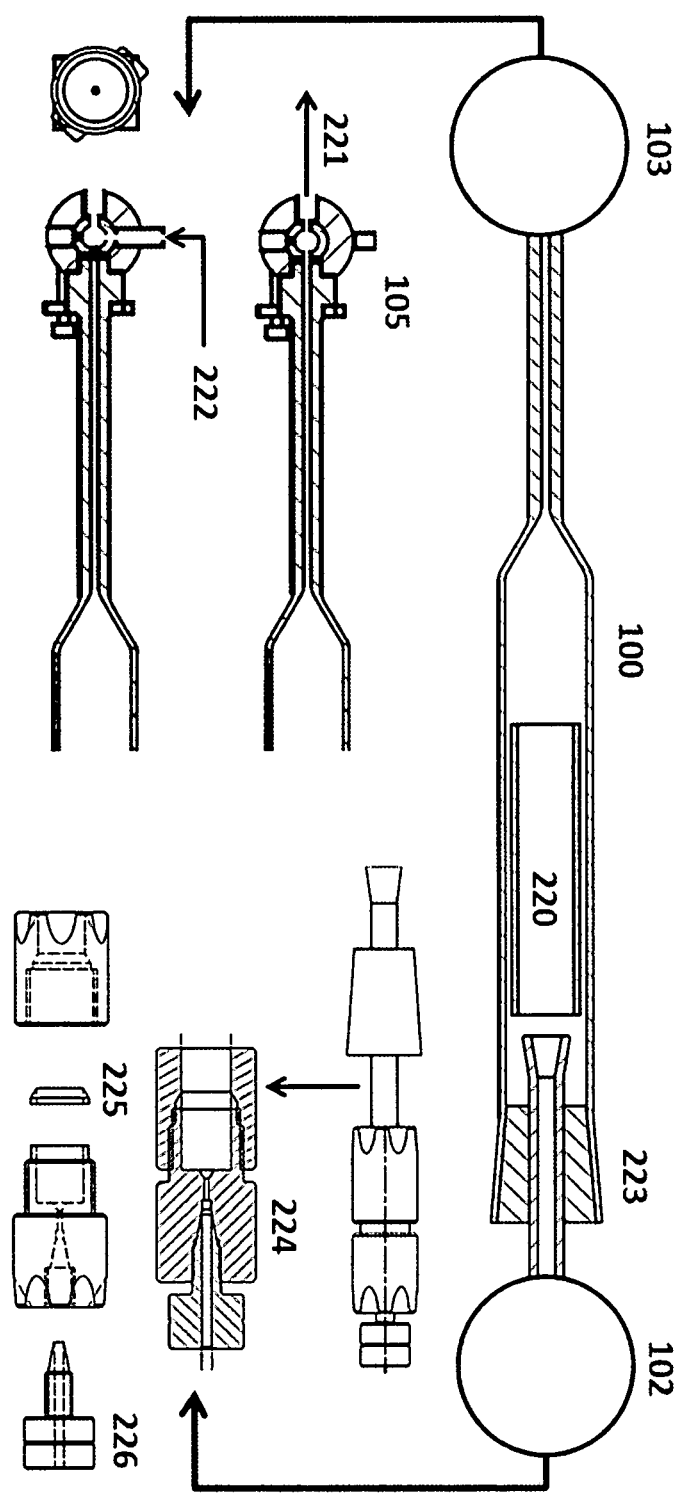
FIG. 2A schematically illustrates a portion of the distillation system illustrated in FIG. 2 including a quartz glass ware and joints for astatine distillation.

FIG. 2A and FIG. 2A:1 illustrates in detail the distillation glassware of the process platform.

Astatine-211 is inserted at the quartz glass receptacle inlet 102 in target material container 220 that can be an open ended quartz glass tube, via back end joint 223. In another embodiment, the inlet joint 223 is fused with the target material container 220 rendering target material container 220 A with cut-out open end joined with a flow through quartz glass cone joint, as shown in FIG. 2A:1. This two-way functional joint reduces the handling of target material and reduces time needed between target material insertion in the pre-heated quartz glass oven and start of distillation. In FIG. 2A:1 an assembly of target material container 220 A and quartz glass receptacle 100 is also shown in 220 B (outside) and 220 C (cross section). A ratio between an outer diameter (OD) of the target material container 220 or 220 A and an inside diameter (ID) is preferably more than 1.8 to 1.

The different positions of three-way valve 105 (FIG. 2A) is 221, allowing for astatine distillation i.e. passage of evaporated astatine through the valve into the condensation capillary by the means of reduced pressure and carrier gas flow and 222, allowing for and the safe introduction of astatine transfer liquid for rinsing the valve and condensation capillary in close proximity to the heated quartz glass receptacle. The valve prevents the transfer liquid entering into the heated receptacle, thereby increasing safety and minimizing activity loss. In a preferred embodiment, the valve is motor driven and software controlled.

Details in FIG. 2A also illustrates the gas tight glassware-capillary connection 224 between the back end of cone joint 223 or similarly the back end of target material container 220 A with a capillary for carrier gas flow. The two back ends of 223 and 220 A are equipped with a glass tube, having an OD (outside diameter) that is equal to an ID (inside diameter) of the glassware-capillary connection 224. Said connection is sealed with a chemically inert packing, such as Teflon, as a non-limiting example 225. In a preferred embodiment, OD and ID are the same and between 6 and 10 mm, or between 7 and 9 mm, or about 8 mm. The capillary is inserted using a finger tight screw joint 226. The connection can be adapted for capillaries having an OD between 1.5-3.2 mm or ¹⁄₁₆"-⅛". In a preferred embodiment, the OD is 3.18 mm. The connection is made of a mechanically stable material. The material use for the heating in the furnace is preferably quartz glass. The material used for capillary joints are preferably heat resistant and non-conducting material, such as PEEK (Polyether Ether Ketone), as a non-limiting example.

The evaporated astatine is condensed using a software controlled cooling unit 106. A cryotrap is an example of a cooling unit. The At-211 is condensed as a dry residue in a chemically inert and flexible capillary 104. Examples of material that can be used for such capillaries may be FEP (Fluorinated Ethylene Propylene) and PFA (Per Fluoro Alkoxy). The capillary 108 may have an OD between 1.5 and 1.7 mm, or about ¹⁄₁₆" and an ID between 0.5 and 1 mm.

Figure 2B:
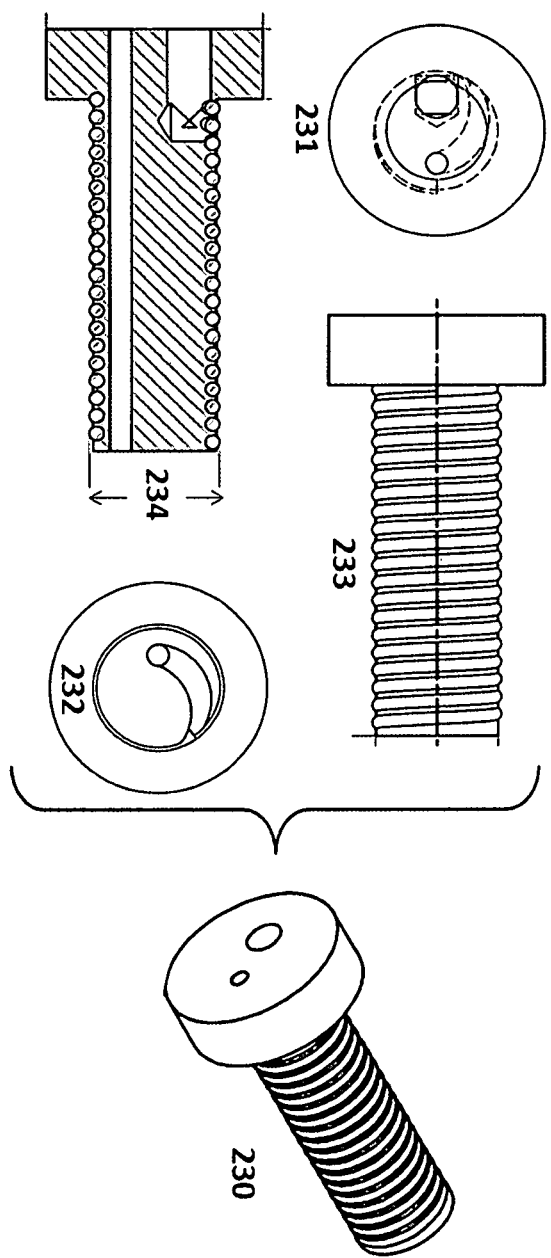
FIG. 2B schematically illustrates a portion of the distillation system illustrated in FIG. 2. Heat transfer insertion for cryotrap.

The cooling unit 106 has the ability for cooling and heating at temperatures between −60° C. and heat +80° C., or between −40° C. and heat +60° C. Electricity may be used for heating. A natural cooling liquid 206, such as liquid nitrogen (transported using vapor pressure) may be used for cooling. Cooling may also be performed using electrical refrigeration of a recirculating coolant. FIG. 2B shows an embodiment of a solid heat transfer insertion 230 for the cryotrap made of a heat conducting material, preferably with thermal conductivity >200 W·m$^{-1}$·K$^{-1}$, such as aluminum or copper as non-limiting examples for cooling/heating a 1.5 to 1.7 mm or about 1/16" OD capillary. The condensation capillary 104 is threaded through the insertion from the top part 231 to the bottom part 232 and then coiled around the outer surface 233 before going through the top part 231 again. For efficient indirect cooling/heating, a ratio of a heat transfer insertion OD 234, including the condensation capillary 104, to an ID of the cooling unit is preferably more than 1.9:1.

The process and platform for performing the process allows fast and repeatable remote controlled astatine distillation with short target material heating times, preferably shorter than 1 minute, followed by pressure equalization, preferably within less than 5 minutes, enabling fast delivery of astatine in a chemically useful form (ready for labeling synthesis), preferably within 8 minutes, from insertion of the target material into the oven.

FIG. 3 shows detail from FIG. 1 describing one embodiment of the astatine labeling chemistry part of the automatic process. In the reaction vial 109, condensed astatine is collected via elution through the condensation capillary 104. Elution is performed with an appropriate organic astatine transfer liquid stored in a container 107. The transfer media is introduced to the distillation three way valve 105 (position 222 in FIG. 2A) and the condensation capillary 104 via a chemically inert capillary 108 using a software controlled inert carrier gas flow such as nitrogen, argon or helium with possible flow rates of 3-50 ml/min. To the reaction vial an underpressure capillary 204 is also connected to allow for the creation of underpressure in the system using a vacuum pump 201 (FIG. 2) as well as a reagent capillary 112 for introduction of labeling reagents stored in n sealed containers 111 V$_{tot}$=0.1-5 ml). In the preferred embodiment those of the containers 111 that allow for introduction of liquid volumes down to 0.1 ml with high surface tension (>70 mN·m$^{-1}$) should preferably render liquid losses below 15 volume % realized by <4 cm of 1/4" FEP capillary, as a non-limiting example. Labeling reagents can be introduced to the reaction vial using software controlled carrier gas flow from gas flow device 208 (shown in figure), underpressure via underpressure capillary 204 or syringe dispenser 300. Labeling reagent flow can be measured via flow sensor 302. The software controlled syringe dispenser should in the preferred embodiment have 2-10 inlet/outlet gates. To the reaction vial another capillary 114 is connected allowing for product transport to purification column 113 using either syringe dispenser 300 (shown in figure), carrier gas flow or underpressure. The purification column would be chosen to fit the produced product such as e.g. gel filtration for proteins and larger peptides and be possible to operate continuously with preferable flow rates between 0.5-10 ml/min. In conjunction to the column there are n containers for purification buffers 117 and reagents introduced on column using either dispenser 300 (shown in figure), carrier gas flow or underpressure. For column discard liquids there is also a waste container 301. Between the column 113 and the final product vial 118 there is an option for sterile filtration 115 of the product, which can be introduced into the product vial using syringe dispenser 300 (shown in figure), software controlled carrier gas flow or underpressure. All liquids and gases in the system are transported via n number of software controlled three way valves 205.

At-211 activity levels during operation of the automatic process platform can optionally be monitored on-line during the distillation process as well as during the labeling and purification process. The measurement can be performed by radioactivity detectors connected to the control unit 140. The activity detectors may be silicon PIN diodes and can be used to regulate both distillation and synthesis part of the automatic process platform through the setting of boundary conditions, such as, but not limited to, maximum or minimum activity, in the software. In FIG. 4 one embodiment is shown where four radioactivity detectors 400, 401, 402 and 403 are used to monitor the distillation process described in FIG. 2 as well as the synthesis and purification process described in FIG. 3. The radioactivity detectors are placed a) 400 close to the reaction vial 109, b) 401 on the condensation capillary 104 close to the cooling unit 106, c) 402 close to the product vial and d) 403 close to the purification column 113. FIG. 4 also show the placement of one radioactivity detector 404 at the inlet of the furnace system 102 which can be used to start the entire distillation process when the At-211 powder is entered into the quartz glass receptacle 100 and the detector hence measures the radioactivity of the At-211 powder.

Several features used in the process of the invention are commercially available items. Some examples are listed below.

Tube furnace: Carbolite® model MTF 10/25/130
Synthesis module: Hot Box III, Scintomics. Including (software controlled):
  20 three way valves
  liquid nitrogen cooling
  gas flow control
Vacuum pump: N810FT Laboport, KNF (controlled by synthesis module software)
Automation Method The following examples are provided to illustrate certain embodiments of the invention, and are not to be construed as limiting the scope of the invention disclosed herein.

Example 1

One example of an embodiment of the invention is automatic, software controlled astatine dry distillation from target material removed from backing and delivery of astatine in a chemically useful form for further processing in an automatic labeling synthesis or manual handling.

Target material typically containing around 550 MBq At-211 produced from alpha particle irradiation (28 MeV) of Bi-209 was removed from the target backing. The quartz glass oven was heated in the tube furnace 101 to 700° C. with the three way valve 105 on outlet in flow through position (detail 221, FIG. 2A), sealing the inlet from the astatine transfer media capillary 108, and inlet glass plug in place allowing for gentle nitrogen flow (20 ml/min) to heat external parts of the quartz glass receptacle 100. Simultaneously the cryotrap was cooled to −50° C. using liquid nitrogen. Liquid and gaseous nitrogen flows were software controlled. Upon removal and refitting of the quartz glass oven inlet plug and insertion of the open-ended quartz glass container with target material in between, the automatic astatine dry distillation and condensation was started. The software starts the vacuum pump reducing pressure in the system while nitrogen flow was increased to 50 ml/min. Also activity monitoring using software controlled activity detectors are started (see FIG. 4—diagram for example). Distillation times were kept short <60 s (typically 25-35 s) and the vacuum pump was turned off resulting in a final reduced pressure between −0.3 and −0.4 Bar. Nitrogen flow was maintained at 20-50 ml/min for 4-5 minutes in order to equalize pressure in the system before eluting the cryotrap condensation capillary. Upon pressure equalization the three way valve was set to elution position (detail 222, FIG. 2A) and the astatine transfer liquid ($V_{tot}$=120 µl, stored in closed container 107) is introduced, via a module valve 205, to the condensation capillary using a gentle nitrogen flow (5-10 ml/min) and collected in the reaction vial 109. The transfer liquids used were chloroform ($CHCl_3$) and a methanol solution with 0.4% acetic acid and 8 µg/ml N-Iodo succinimide (MeOH/NIS). See Table 1.

TABLE 1

Automatic dry distillation of At-211 and delivery of astatine in a chemically useful form using the automatic process platform herein described

| Target material activity (MBq) | Elution media | Distillation Yield (%) |
|---|---|---|
| 626 | MeOH/NIS | 87 |
| 594 | $CHCl_3$ | 85 |
| 572 | MeOH/NIS | 88 |
| 593 | $CHCl_3$ | 90 |
| 442 | MeOH/NIS | 92 |
| 623 | $CHCl_3$ | 91 |

Example 2

One example of an embodiment of the invention is automatic, software controlled astatine labeling of ATE-modified antibodies (antibodies with attached N-succinimidyl-3-(trimethylstannyl)benzoate molecules on lysine residues of the antibody to allow for astatodestannylation reactions) according to FIG. 3 using astatine in a chemically useful form produced in the automatic distillation part of the process platform according to FIG. 2. Depending on the astatine transfer media used the synthesis can be performed in different ways.

Case 1: With an astatine transfer media ($V_{tot}$=120 µl) consisting of a methanol solution with 0.4% acetic acid and 8 µg/ml N-Iodo succinimide (NIS) as oxidant the astatine can be eluted directly into a solution of the conjugated precursor molecule, in this case ATE-modified antibody Trastuzumab or MX35 ($V_{tot}$=520 µl, 1 mg/ml, previously automatically introduced into the reaction vial) immediately starting the labeling reaction. After a reaction time of 1 min where agitation was facilitated using nitrogen gas bubbling the reagents needed to remove residual tin groups and quenching the reaction was introduced with a 1 minute reaction time for tin removal using NIS in citrate buffer (pH 5.5) with 3% methanol (with 1% acetic acid) ($V_{tot}$=110 µl) and 30 s for quenching using sodium ascorbate (6 mg/ml) ($V_{tot}$=110 µl).

Case 2: If the astatine transfer media used is chloroform, the chloroform has to be evaporated before starting the reaction. This can be done by the automatic process platform within 10 minutes for a 300 µl chloroform residue using reduced pressure or heat and nitrogen gas flow resulting in activity losses <10%. In this case the oxidizing methanol solution with 0.4% acetic acid and 8 µg/ml NIS ($V_{tot}$=120 ul) has to be added to the dry astatine residue in the reaction vial (reaction time 30 s) prior to introduction of the conjugated precursor molecule, in this case ATE-modified antibody Trastuzumab ($V_{tot}$=520 ul, 1 mg/ml). The following reactions are the same as in Case 1.

Reagent introductions were in both cases facilitated using a gentle nitrogen flow of 5-15 ml/min from sealed reagent containers (107, 111) via three way valves 205. The product was then either manually purified using a NAP10 (Sephadex G25, GE Healtcare) column or using the automatic setup with a HiTrap Desalting (Sephadex G25, GE Healtcare) flow through column or a PD10 gravity column.

TABLE 2

Astatine labeling using automatic process platform of already prepared ATE-conjugated antibody Trastuzumab

| Initial activity (MBq) | Elution medium | Conjugated Antibody | Purification Method | Labelling yield (%) | Radiochemical Purity (%) | Specific activity (MBq/mg) |
|---|---|---|---|---|---|---|
| 509 | MeOH/NIS | Trastuzumab | Manual Nap10 | 55 | 97 | 560 |
| 456 | MeOH/NIS | Trastuzumab | Automatic HiTrap | 48 | 99 | 430 |
| 400 | MeOH/NIS | MX35 | Automatic PD10 | 56 | 95 | 446 |
| 219 | $CHCl_3$ * | Trastuzumab | Manual Nap10 | 64 | 96 | 280 |
| 215 | $CHCl_3$ * | Trastuzumab | Automatic HiTrap | 55 | 98 | 230 |

* $CHCl_3$ evaporated using process platform before start of synthesis

| Feature | Reference number |
|---|---|
| Quartz glass receptacle | 100 |
| Tube furnace | 101 |
| Quartz glass receptacle inlet | 102 |
| Quartz glass receptacle outlet | 103 |
| Condensation capillary | 104 |
| Three way valve | 105 |
| Cooling unit | 106 |
| Transfer liquid container | 107 |
| Transfer liquid capillary | 108 |
| Reaction vial | 109 |
| Reagent container(s) | 111 |
| Reagent capillary | 112 |
| Purification unit | 113 |
| Purification capillary | 114 |
| Sterile filter | 115 |
| Filtration capillary | 116 |
| Purification buffer | 117 |
| Product vial | 118 |

-continued

| Feature | Reference number |
|---|---|
| Scraping unit | 120 |
| Target | 121 |
| Target holder | 122 |
| Chisel | 123 |
| Motor | 124 |
| At-211 powder | 125 |
| Computer | 130 |
| Control Unit | 140 |
| Gas flow capillary | 200 |
| Vacuum Pump | 201 |
| Moisture absorption media | 202 |
| Astatine traps | 203 |
| Underpressure capillary | 204 |
| Software controlled valves | 205 |
| Cooling media | 206 |
| Pressure sensor | 207 |
| Gas flow device | 208 |
| Target material container | 220 |
| Target material container with back end joint | 220 A |
| Assembly of 220 A and 100 (outside) | 220 B |
| Assembly of 220 A and 100 (cross section) | 220 C |
| Three way valve distillation position | 221 |
| Three way valve elution position | 222 |
| Back end joint for target material container | 223 |
| Glassware-capillary connection | 224 |
| Packing - detail of 124 | 225 |
| Screw joint - detail of 224 | 226 |
| Heat transfer insertion | 230 |
| Top of heat transfer insertion | 231 |
| Bottom of Heat transfer insertion | 232 |
| Outer surface of Heat transfer insertion | 233 |
| OD of Heat transfer insertion plus 104 | 234 |
| Syringe dispenser | 300 |
| Waste container | 301 |
| Flow sensor | 302 |
| Radioactivity detector 1 | 400 |
| Radioactivity detector 2 | 401 |
| Radioactivity detector 3 | 402 |
| Radioactivity detector 4 | 403 |
| Radioactivity detector 5 | 404 |

The invention claimed is:

1. An automatic system for controlling a process for production of At-211-labeled molecules from target material containing At-211 in solid form, characterized in that the automatic system comprises:
a scraping unit (120) for scraping an irradiated bismuth target to At-211 powder (125) target material,
a receptacle (100) for receiving a powder of At-211,
a furnace (101) for vaporization of the At-211 powder by heating the receptacle (100),
a cooling unit (106) for indirectly condensing the vaporized At-211 to obtain At-211 as a dry residue in condensation capillary (104) coiled around heat transfer insertion (230),
a transfer liquid container (107) containing a transfer liquid for eluting the At-211,
a reaction vial (109) for further chemical processing of the At-211,
a three way valve (105) connecting the receptacle (100) with a capillary system including a plurality of capillaries comprising condensation capillary 104 and transfer liquid capillary (108) for transportation of the vaporized At-211 to the cooling unit (106) and further to the reaction vial (109), and for transportation of the transfer liquid from the liquid container (107) to the cooling unit (106),
a vacuum pump (201) arranged to reduce the pressure in the condensation capillary (104), reaction vial (109) and receptacle (100) to achieve an underpressure in the automatic system for transportation of the At-211,
valves (205) for transport of transfer liquid and further chemical processing of the At-211,
a capillary (112) for transportation of reagent from a reagent container (111) to the reaction vial (109),
a gas flow device (208) arranged to introduce a gas flow into the receptacle (100), and into a capillary and valve system comprising, for distillation, capillaries (104, 108) and three way valve (105), and for synthesis, reagent capillary (112) and valves (205) for assisting in transportation of the At-211, the transfer liquid, reagents and solvents,
one or more radioactivity detectors (400, 401, 402, 403, 404) for measuring the radioactivity at one or more locations in the automatic system, and
one control unit (140), the control unit (140) configured to control the transportation of the At-211, the transfer liquid, reagents and product in the capillary and valve system by generating control commands to the vacuum pump and the gas flow device based on input data from the radioactivity detectors corresponding to measured radioactivity at said one or more locations in the automatic system.

2. The system according to claim 1, wherein the control unit is configured to generate the control commands to the vacuum pump (201) and the gas flow device (208) based on the input data from the radioactive detectors (400, 401, 402, 403, 404) and predefined limit values for the radioactivity at said locations in the system.

3. The system according to claim 1, wherein the system further comprises at least one pressure sensor (206) for sensing the pressure in the capillary system, and the control unit (140) is configured to generate the control commands to the vacuum pump (201) based on input data from the radioactive detectors and input data from the at least one pressure sensor.

* * * * *